US009533029B2

(12) United States Patent
Finzi

(10) Patent No.: US 9,533,029 B2
(45) Date of Patent: *Jan. 3, 2017

(54) METHOD OF TREATING DEPRESSION

(71) Applicant: Eric Finzi, Chevy Chase, MD (US)

(72) Inventor: Eric Finzi, Chevy Chase, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/746,299

(22) Filed: Jun. 22, 2015

(65) Prior Publication Data

US 2015/0290302 A1 Oct. 15, 2015

Related U.S. Application Data

(63) Continuation of application No. 13/789,216, filed on Mar. 7, 2013, now Pat. No. 9,060,964, which is a continuation of application No. 12/813,373, filed on Jun. 10, 2010, now Pat. No. 8,414,902, which is a continuation of application No. 10/773,785, filed on Feb. 6, 2004, now Pat. No. 7,758,872.

(60) Provisional application No. 60/445,868, filed on Feb. 7, 2003.

(51) Int. Cl.
*A61K 38/48* (2006.01)
*A61K 39/08* (2006.01)
*A61K 45/00* (2006.01)
*A61K 45/06* (2006.01)

(52) U.S. Cl.
CPC .......... *A61K 38/4893* (2013.01); *A61K 39/08* (2013.01); *A61K 45/00* (2013.01); *A61K 45/06* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 5,714,468 A | 2/1998 | Binder | |
| 6,358,917 B1 | 3/2002 | Carruthers et al. | |
| 7,758,872 B1* | 7/2010 | Finzi | A61K 38/4893 424/236.1 |
| 7,846,457 B2 | 12/2010 | Steinsapir | 424/247.1 |
| 8,414,902 B2* | 4/2013 | Finzi | A61K 38/4893 424/236.1 |
| 8,501,195 B2 | 8/2013 | Turkel et al. | 424/239.1 |
| 8,609,112 B2 | 12/2013 | Blumenfeld et al. | 424/247.1 |
| 8,609,113 B2 | 12/2013 | Blumenfeld et al. | 424/247.1 |
| 8,617,572 B2 | 12/2013 | Blumenfeld | 424/247.1 |
| 8,734,810 B2 | 5/2014 | Blumenfeld | 424/239.1 |
| 8,940,308 B2* | 1/2015 | Turkel | A61K 38/164 424/236.1 |
| 9,050,246 B2* | 6/2015 | Bertholon | A61K 9/0014 |
| 9,060,964 B2* | 6/2015 | Finzi | A61K 38/4893 |
| 9,254,314 B2* | 2/2016 | Finzi | A61K 38/4893 |
| 2010/0249036 A1 | 9/2010 | Finzi | 514/17.6 |
| 2013/0142776 A1 | 6/2013 | Blumenfeld | 424/94.67 |
| 2013/0142777 A1 | 6/2013 | Blumenfeld | 424/94.67 |
| 2013/0150307 A1 | 6/2013 | Turkel et al. | 514/17.6 |
| 2013/0189307 A1 | 7/2013 | Finzi | 424/239.1 |
| 2013/0224180 A1 | 8/2013 | Turkel et al. | 424/94.67 |
| 2013/0330321 A1 | 12/2013 | Turkel et al. | 424/94.67 |
| 2014/0030249 A1* | 1/2014 | Duffield | A61K 9/0004 424/94.67 |
| 2014/0099298 A1* | 4/2014 | Blumenfeld | A61K 38/4893 424/94.67 |
| 2014/0205590 A1* | 7/2014 | Blumenfeld | A61K 9/0019 424/94.67 |
| 2015/0086532 A1* | 3/2015 | Borodic | A61K 38/4893 424/94.67 |
| 2015/0086533 A1* | 3/2015 | Borodic | A61K 38/4893 424/94.67 |
| 2015/0132282 A1* | 5/2015 | Finzi | A61K 31/00 424/94.67 |
| 2015/0132283 A1* | 5/2015 | Borodic | A61K 38/4893 424/94.67 |
| 2015/0165003 A1* | 6/2015 | Jung | A61K 8/66 424/94.67 |
| 2015/0258183 A1* | 9/2015 | Borodic | A61K 38/4893 424/94.67 |
| 2015/0290302 A1* | 10/2015 | Finzi | A61K 38/4893 424/94.67 |
| 2015/0297688 A1* | 10/2015 | Borodic | A61K 38/4893 424/9.2 |
| 2016/0045577 A1* | 2/2016 | Borodic | A61K 38/4893 424/94.67 |
| 2016/0051643 A1* | 2/2016 | Borodic | A61K 38/4893 424/94.67 |
| 2016/0114015 A1* | 4/2016 | Finzi | A61K 38/4893 424/94.67 |

OTHER PUBLICATIONS

Magid et al, Pharmacopsychiatry 2015; 48: 205-210.*
Bedarf et al, Movement Disorders, (Jun. 2015) vol. 30, Supp. Suppl. 1, pp. S499. Abstract No. 1282. Meeting Info: 19th International Congress of Parkinson's Disease and Movement Disorders. San Diego, CA, United States. Jun. 14, 2015-Jun. 18, 2015 (abstract only).*
Finzi et al, Journal of Psychiatric Research 52 (2014) 1-6.*
Hawlik et al, Fortschritte der Neurologie-Psychiatrie, (Feb. 2014) vol. 82, No. 2, pp. 93-99. Electronic Publication Date: Feb. 11, 2014, Journal code: 8103137. E-ISSN: 1439-3522. L-ISSN: 0720-4299. (abstract only).*
Kruger et al, Abstract # O-29—Botulinum Neurotoxin for Treatment of Depression, 20th European Congress of Psychiatry, European Psychiatry, 2012, vol. 27, Suppl. 1 (abstract only).*
Adelmann et al., "Facial efference and the experience of emotion," *Ann. Rev. Psychol*, 40:249-280 (1989).
Brenner et al., "Acute anxiety and depression induced by loss of sensation and muscle control after botulinum toxin A injection," *South Med J* 92(7):738 (1999).
Cohen, "Rational drug use in the treatment of depression," Pharmacotherapy 17(1):45-61 (Jan.-Feb. 1997) (Abstract only).

(Continued)

Primary Examiner — Nita M Minnifield
(74) Attorney, Agent, or Firm — Brigitte C. Phan; Ted A. Chan

(57) ABSTRACT

Methods are disclosed herein for treating depression in the subject. A method includes the use of *Botulinum* toxin to cause paralysis of a facial muscle, such as the depressor anguli oris, procerus, frontalis, orbicularis oculi, or corrugator supercilii muscle to treat depression in the subject.

11 Claims, 6 Drawing Sheets

(56) References Cited

OTHER PUBLICATIONS

Cole, *About Face*, The MIT Press, Massachusetts Institute of Technology, Cambridge, MA (1998).
Darwin, The expression of the emotions in man and animals, *University of Chicago Press*, Chicago, IL, 1965, as shown at: http://pages.britishlibrary.net/charles.darwin3/espression/expression_intro.htm, (Dec. 28, 2002).
Finzi and Wasserman, "Treatment of depression with Botulinum Toxin A: A Case Series," *Dermatologic Surgery* 32(5):645-650 (2006).
Gudex et al., "Effect of dystonia and botulinum toxin treatment on health-related quality of life," *Mov. Disord* 13(6):941-946 (1998) (Abstract only).
Heckmann et al., "Pharmacologic denervation of frown muscles enhances baseline expression of happiness and decreases baseline expression of anger, sadness, and fear," *J. Am. Acad. Dermatol.* 49(2):213-216 2003 (Abstract only).
Jahanshahi et al., "Psychological functioning before and after treatment of torticollis with botulinum toxin," *Journal of Neurology, Neurosurgery and Psychiatry* 55:229-231 (1992).
Muller et al., "The impact of blepharospasm and cervical dystonia on health-related quality of life and depression," *J. Neurol.* 249(7):842-846 (2002) (Abstract only).
Murry et al., "Spasmatic dysphomia, emotional status and Botulinum Toxin Treatment," *Arch Otolaryngol Head Neck Surg* 120:310-316 (Mar. 1994).
Wagstaff et al., "Paroxetine: an update of its use in psychiatric disorders in adults," *Drugs* 62(4):655-703 (2002) (Abstract only).
Finzi et al, Dermatol Surg 2006;32:645-650.
Cassels, "More Evidence Botox Works for Depression"; Medscape Medical News, Jun. 2014, http://www.webmd.com/depression/news/20140619/botox-depression.
Jahanshahi et al, J. Neurology, Neurosurgery and Psychiatry, 1992, 55:229-231.
Brenner et al, southern Medical Journal, Jul. 1999, 92/7:738 abstract only.
Finzi et al, Neuropsychopharmacology, Dec. 2012, vol. 38, Suppl. Suppl. 1, pp. S316 abstract only.
Wagstaff et al, Drugs, 2002, 62/4:655-703 abstract only.
Fried et al, J. Clinical and Aesthetic Dermatology, Nov. 2009, 2/11:37-40.

\* cited by examiner

METHOD OF TREATING DEPRESSION

CROSS-REFERENCE TO RELATED APPLICATIONS

This is a continuation of U.S. application Ser. No. 13/789,216, filed Mar. 7, 2013, now U.S. Pat. No. 9,060,964, which is a continuation of U.S. application Ser. No. 12/813,373, filed on Jun. 10, 2010, now U.S. Pat. No. 8,414,902, which is a continuation of U.S. patent application Ser. No. 10/773,785, filed on Feb. 6, 2004, now U.S. Pat. No. 7,758,872, which in turn claims the benefit of U.S. Provisional Application No. 60/445,868, filed Feb. 7, 2003. All of the prior applications are incorporated by reference herein in their entirety.

FIELD

This application relates to the field of psychiatry. In particular, this application pertains to the discovery that agents that affect the movement of the facial muscles, such as botulism toxin, can be used in methods of ameliorating depression.

BACKGROUND

The mood and anxiety disorders in their various permutations constitute a major source of personal suffering and impaired ability to engage in productive work and interpersonal relationships. Between 5 and 9% of women and between 2 and 3% of men meet the diagnostic criteria for major depression at any time; 10-25% of all women suffer major depression sometime in their lives, while 5-10% of men will develop major depressive disorder (American Psychiatric Association, 1994).

Affective disorders, while characterized by depressed mood of varying degrees, exist in various forms. The various forms of depression are defined and are separately diagnosed according to criteria given in handbooks for psychiatry, for example in the *Diagnostic and Statistical Manual of Mental Disorders* 4th edition (DSM-IV) published by the American Psychiatric Association, Washington, D.C. (1994). In the DSM-IV, depressive disorders are classified under mood disorders and are divided into three types: major depressive disorder, dysthymic disorder and depressive disorder not otherwise specified (or "atypical"). In general, regardless of whether or not the depressive syndrome is melancholic, atypical, or some admixture of the two, a diagnosis of major depression is given when depressed mood is present, or loss of interest or pleasure in all activities is present, for at least two weeks.

Thus, melancholic depression is characterized by continuously depressed mood and pervasive hopelessness, insomnia with early-morning awakening (with the inability to return to sleep), loss of appetite and weight loss, and excessive feelings of guilt. In contrast, so-called "atypical" depression is characterized by hypersomnia (oversleeping), hyperphagia and weight gain, and—often—mood reactivity.

Major depressive disorder and dysthymic disorder are differentiated based on chronicity, severity and persistence. If less severe or incapacitating, depressed mood is considered dysthymia. Depressed mood can occur in the form of a cycling mood abnormality such as bipolar mood disorder, cyclothymia, or menstrual-related mood disorder. In dysthymic disorder the depressed mood must be present most days over a period of two years.

Usually, major depressive disorder is characterized by its sharp contrast to usual functioning. A person with a major depressive episode can be functioning and feeling normal and suddenly develop severe symptoms of depression. By contrast, a person with dysthymic disorder has chronic depression with less severe symptoms than major depression. Major depression is a major health problem and poses a tremendous financial burden on society due to lost self-support of individuals suffering from depression. Such individuals are often simply unable to function in everyday life situations, in part because of feelings of extreme hopelessness and worthlessness. There is also a serious risk of suicide among such individuals. The diagnostic criteria for major depression are well known to those skilled in the art, and comprise the criteria set forth, for example, at DSM-IV 296.2 and 296.3.

Psychotic major depression has long been recognized as a distinct psychiatric illness, having both psychotic and depressive components. In a differential diagnosis, it is important that psychotic major depression be distinguished from non-psychotic major depression, because effective treatments and patterns of response to pharmacologic therapies for psychotic major depression are often different from those relating to non-psychotic major depression. Successful treatment depends on the accuracy of the initial diagnosis. (Glassman, *Arch. Gen. Psychiatry* 38:424-427, 1981, Schatzberg, *Am. J. Psychiatr.* 149:733-745, 1992, Schatzberg, *Annals N.Y. Acad. of Sci.* 537:462, 1988). Psychotic major depression is very common It has been estimated that twenty five percent of depressed patients admitted to the hospital have psychotic major depression (Coryell *Nerv. Ment. Dis.* 172:521, 1984).

Mood and anxiety disorders very frequently coexist in the same individual. In this regard, it is now appreciated that almost all antidepressants improve anxiety symptoms. Conversely, the most popular anxiolytics, the benzodiazepines, improve mood acutely but are typically ineffective or harmful to mood during chronic use.

The current psychopharmacologic treatments of affective and anxiety disorders have certain drawbacks. A significant portion of depressed patients are resistant to treatment with existing antidepressants or combinations thereof either because of non-responsiveness or because a positive effect wears off (breakthrough depression) or is inadequate (depression in partial remission). Troubling side effects, such as gastrointestinal disturbances or loss of libido, may also be seen with existing antidepressants. Moreover, current psychopharmacologic anti-depressants have a latency of typically two weeks before the onset of significant antidepressant activity. The most commonly used anxiolytic medications, the benzodiazepines, have a number of major limitations: (a) tolerance to their effects rapidly develops, with increasing doses becoming required to achieve the same effect; (b) benzodiazepine dependence is a standard occurrence after chronic use; (c) major withdrawal syndromes are seen—including grand mal seizures—after abrupt discontinuation; (d) overdose is associated with respiratory depression and sometimes death; (e) effects are potentiated by alcohol, which is cross-tolerant with the benzodiazepines; and (f) high abuse potential.

Depression is often associated with psychomotor abnormalities, such as increased or retarded motor activity. Many depressed persons can also be recognized by their "depressed facies" in which the muscles of facial expression assume a distressed or sad appearance. For example, the brow may be furrowed, the inner ends of the eyebrows raised, and the angles of the mouth lowered such that the facial appearance is recognizably sad and/or anxious.

Although treatments for different types of depression do exist, there is a continuous search for new methods of treatment. Existing therapeutic approaches still have disadvantages, such as the side effects of drugs, the long duration of treatments, and more importantly, the partial efficacy (or inefficacy) of existing treatments. Although some existing treatments are effective, there is still a need for alternative treatments, or therapeutic approaches that can be used in combination with existing treatment modalities.

SUMMARY OF THE INVENTION

A method is provided herein for treating depression. The method includes administering to a person with an affective disorder a therapeutically effective amount of drug that interferes with the ability of the facial muscles to assume a depressed facies. For example, a neurotoxin is administered to a facial muscle involved in frowning or scowling. The neurotoxin affects the ability of the subject to frown and/or scowl, thereby treating depression. In one such method, a therapeutically effective amount of *Botulinum* toxin A can be injected into one or more of the frontalis, procerus, the corrugator supercilii, orbicularis oculi, or the depressor anguli oris (trianglaris muscle). Four major muscle groups are involved in frowning: the frontail, procerus, corrugator supercilii and orbicularis oculi (Weider et al. *Derm Surg.* 24:1172-1174, 1998. The corrugator supercilii is also known as the "scowl" muscle. In a particular example, the *Botulinum* toxin A is injected into the procerus muscle over the glabella.

The foregoing and other features and advantages will become more apparent from the following detailed description of several embodiments, which proceeds with reference to the accompanying figures.

DETAILED DESCRIPTION OF THE PREFERRED EMBODIMENTS

Figure 1:
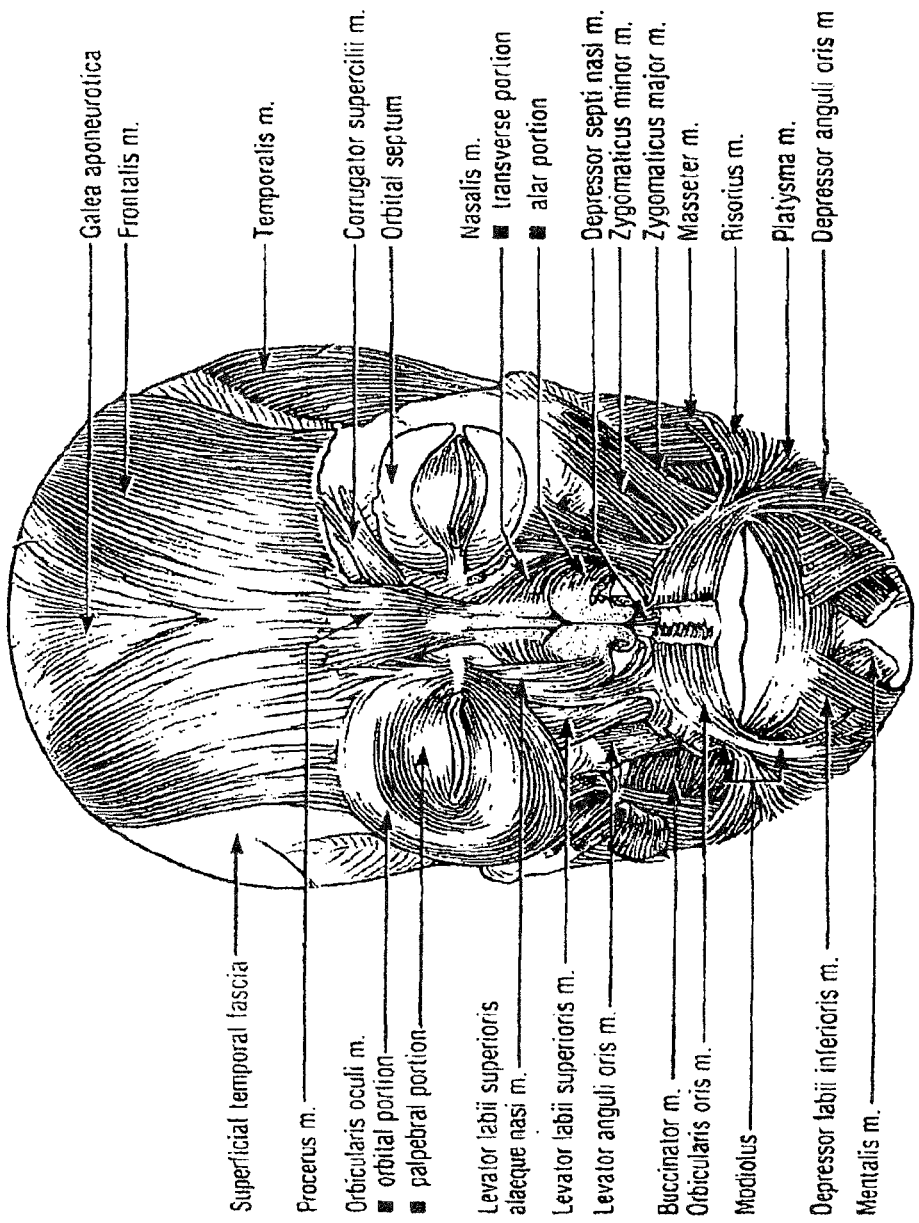
FIG. 1 is a schematic diagram of a frontal view of the musculature of the human face and neck. Injection sites for a neurotoxin, including the frontalis, procerus, the corrugator supercilii, orbicularis oculi, or the depressor anguli oris muscles are shown.

I. Abbreviations
   BTX: *Botulinum* toxin
   U: Units
II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Ameliorating or ameliorate: Any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation. For example, a clinical guide to monitor the effective amelioration of a psychiatric disorder, such as depression, is found in the Structured Clinical Interview for DSM-IV Axis I mood disorders ("SCID-P") (see fourth edition of *Diagnostic and Statistical Manual of Mental Disorders* (1994) Task Force on DSM-IV, American Psychiatric Association ("DSM-IV"); Kaplan, Ed. (1995); *Comprehensive Textbook of Psychiatry/VI*, vol. 1, sixth ed., pp 621-627, Williams & Wilkins, Baltimore, Md.).

Anti-Depressant Medications: A pharmaceutical agent that is administered as a treatment for depression. Anti-depressant medications include synthesized chemical compounds as well as naturally occurring or herbal remedies such as St. John's Wort. Generally, these medications are administered orally, but they may also be administered in any form of use to a medical practitioner. Examples of antidepressant medications include tricyclic antidepressants, which generally affect the two chemical neurotransmitters, norepinephrine and serotonin. Tricyclic antidepressants include imipramine, amitriptyline, nortriptyline, and desipramine Monoamine oxidase inhibitors (MAOIs) are also used as antidepressants. MAOIs approved for the treatment of depression include phenelzine (NARDIL®), tranylcypromine (PARNATE®), and isocarboxazid (MARPLAN®). Medications that primarily affect the neurotransmitter serotonin, termed selective serotonin reuptake inhibitors (SSRIs), are also used as antidepressants. These include escitalopram HBr (LEXAPRO®), fluoxetine (PROZAC®), sertraline (ZOLOFT®), fluvoxamine (LUVOX®), paroxetine (PAXIL®), and citalopram (CELEXA®). Additional medication of use affect both norepinephrine and serotonin, for example venlafaxine (EFFEXOR®) and nefazadone (SERZONE®), or agents such as phenelzine (NARDIL®), tranylcypromine (PARNATE®), mirtazepine (REMERON®), nefazodone (SERZONE®), triazolopyridine (TRAZODONE®), and bupropion (WELLBUTRIN®).

Botulinum toxin: A toxin produced by the bacterium *Clostridium botulinum*, but which may either be obtained from a natural source or made by synthetic means. Seven immunologically distinct *Botulinum* neurotoxins have been characterized, these being respectively *Botulinum* neurotoxin serotypes A, B, $C_1$, D, E, F and G, each of which is distinguished by neutralization with type-specific antibodies. The different serotypes of *Botulinum* toxin vary in the animal species that they affect and in the severity and duration of the paralysis they evoke. For example, it has been determined that *Botulinum* toxin type A is 500 times more potent, as measured by the rate of paralysis produced in the rat, than is *Botulinum* toxin type B. Additionally, *Botulinum* toxin type B has been determined to be non-toxic in primates at a dose of 480 U/kg which is about 12 times the primate $LD_{50}$ for *Botulinum* toxin type A (Moyer et al., "*Botulinum* Toxin Type B: Experimental and Clinical Experience," in *Therapy With Botulinum Toxin*, Marcel Dekker, Inc Jankovic et al.(eds.), pgs. 71-85, 1994).

Depression: A mental state of depressed mood characterized by feelings of sadness, despair and discouragement. Depression includes feelings of sadness considered to be normal (mild depression), dysthymia, and major depression. Depression can resemble the grief and mourning that follows bereavement, and there are often feelings of low self esteem, guilt and self reproach, withdrawal from interpersonal contact and somatic symptoms such as alterations in eating habits and sleep disturbances.

Frown: To furrow the brow to show unhappiness or displeasure. This action uses the orbicularis oculi, the frontalis muscle and/or the corrugator supercilii muscle. This action can also include the use of the procerus muscle.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Psychotic: A psychiatric condition in its broadest sense, as defined in the DSM-WV (Kaplan, ed. (1995) supra) and described below. Different disorders which have a psychotic component comprise different aspects of this definition of "psychotic." For example, in schizophreniform disorder, schizoaffective disorder and brief psychotic disorder, the term "psychotic" refers to delusions, any prominent hallucinations, disorganized speech, or disorganized or catatonic behavior. In psychotic disorder due to a general medical condition and in substance-induced psychotic disorder, "psychotic" refers to delusions or only those hallucinations that are not accompanied by insight. Finally, in delusional disorder and shared psychotic disorder, "psychotic" is equivalent to "delusional" (see DSM-IV, supra, page 273).

Objective tests can be used to determine whether an individual is psychotic and to measure and assess the success of a particular treatment schedule or regimen. For example, measuring changes in cognitive ability aids in the diagnosis and treatment assessment of the psychotic patient. Any test known in the art can be used, such as the so-called "Wallach Test," which assesses recognition memory (see below, Wallach, *J. Gerontol.* 35:371-375, 1980). Another example of an objective text that can be used to determine whether an individual is psychotic and to measure efficacy of an anti-psychotic treatment is the Stroop Color and Word Test ("Stroop Test") (see Golden, C. J., Cat. No. 30150M, in *A Manual for Clinical and Experimental Uses*, Stoelting, Wood Dale, Ill.). The Stroop Test is an objective neuropsychiatric test that can differentiate between individuals with psychosis and those without.

Psychosis: A psychiatric symptom, condition or syndrome in its broadest sense, as defined in the DSM-IV (Kaplan, ed. (1995) supra), comprising a "psychotic" component, as broadly defined above. Psychosis is typically defined as a mental disorder or condition causing gross distortion or disorganization of a person's mental capacity, affective response, and capacity to recognize reality, communicate, and relate to others to the degree of interfering with his capacity to cope with the ordinary demands of everyday life.

Psychotic major depression: A condition also referred to as psychotic depression (Schatzberg, *Am. J. Psychiatry* 149:733-745, 1992), "psychotic (delusional) depression," "delusional depression," and "major depression with psychotic features" (see the DSM-III-R). This condition is a distinct psychiatric disorder that includes both depressive and psychotic features. Individuals manifesting both depression and psychosis, i.e. psychotic depression, are often referred to as "psychotic depressives."

Scowl: A facial expression showing displeasure. Scowling primarily utilizes the corrugator supercilii muscle and the procerus muscle.

Subject: Any mammal In one embodiment, a subject is a human subject.

Therapeutically effective amount: A quantity of treatment, such as drug, for example a neurotoxin such as *Botulinum* toxin A, sufficient to achieve a desired effect in a subject being treated. For instance, this can be the amount of *Botulinum* toxin A necessary to impair contraction of, or paralyze, a facial muscle. This can also be the amount of a therapy, such as light therapy or psychotherapy, sufficient to relieve a symptom of a disorder, such as depression. This can also be the amount of an antidepressant sufficient to alter the mood of a subject.

Unit equivalents: An amount of *Botulinum* Toxin (BTX) that is equivalent to standard Units of *Botulinum* Toxin A (BTX-A). A standard Unit of BTX-A is defined as the mean $LD_{50}$ for female Swiss Webster mice weighing 18-20 grams (Schantz and Kaultner, *J. Assoc. Anal. Chem.* 61: 96-99, 1978). The estimated human $LD_{50}$ for a 70-kg person is 40 Units/kg or about 2500-3000 Units.

BOTOX™ (*Botulinum* toxin A, Allergan, Inc., Irvine, Calif., U.S.A.) is sold in 100 Unit vials. DYSPORT™ (Speywood Pharmaceuticals, Ltd., Maidenhead, U.K.) is sold in 500 Unit vials. For cosmetic uses, the vial contents are typically diluted with 1 or 2 ml of sterile saline solution, which for BOTOX™ provides a 100 or 50 Unit/ml dilution. DYSPORT™ BTX-A is roughly tenfold less toxic than BOTOX™ and approximately fourfold greater amounts of the DYSPORT™ product will usually be injected to achieve the same result as would be obtained using a specific number of Units of BOTOX™.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Botulinum Toxin

Botulinum toxin (BTX), produced by the bacterium *Clostridium botulinum* reversibly paralyzes striated muscle when administered in sub-lethal doses. BTX has been used in the treatment in a number of neuromuscular disorders and conditions involving muscular spasm including, but not limited to, dystonia, hemifacial spasm, tremor, spasticity (e.g. resulting from multiple sclerosis), anal fissures and various ophthalmologic conditions (for example, see Carruthers et al., *J. Amer. Acad. Derm.* 34:788-797, 1996). A *Botulinum* toxin type A complex has been approved by the U.S. Food and Drug Administration for the treatment of blepharospasm, strabismus and hemifacial spasm.

BTX is a generic term covering a family of toxins produced by *C. botulinum* comprising up to eight serologically distinct forms (A, B, $C_1$, $C_2$, D, E, F and G). These toxins are among the most powerful neuroparalytic agents known (c.f. Melling et al., *Eye* 2:16-23, 1988). Serotypes A, B and F are the most potent. Without being bound by theory, the mode of action is believed to be an inhibition of the release of acetylcholine by the presynaptic nerve.

*Botulinum* toxin type A can be obtained by establishing and growing cultures of *Clostridium botulinum* in a fermenter and then harvesting and purifying the fermented mixture in accordance with known procedures. Alternatively, the *Botulinum* toxin serotypes are initially synthesized as inactive single chain proteins which must be cleaved or nicked by proteases to become neuroactive. High quality crystalline *Botulinum* toxin type A can be produced from the Hall A strain of *Clostridium botulinum*. The Schantz process can be used to obtain crystalline *Botulinum* toxin type A (see Schantz et al., *Microbiol Rev.* 56; 80-99, 1992). Generally, the *Botulinum* toxin type A complex can be isolated and purified from an anaerobic fermentation by cultivating *Clostridium botulinum* type A in a suitable medium. This process can be used, upon separation out of the non-toxin proteins, to obtain pure *Botulinum* toxins, such as for example: purified *Botulinum* toxin type A with an approximately 150 kD molecular weight, purified *Botulinum* toxin type B with an approximately 156 kD molecular weight and purified *Botulinum* toxin type F with an approximately 155 kD molecular weight.

*Botulinum* toxins and/or *Botulinum* toxin complexes can be obtained from List Biological Laboratories, Inc., Campbell, Calif.; the Centre for Applied Microbiology and Research, Porton Down, U.K.; Wako, Osaka, Japan; Metabiologics, Madison, Wis.) as well as from Sigma Chemicals, St Louis, Mo.

The initial cosmetic use of BTX was for treatment of forehead frown lines as reported in Carruthers and Carruthers, *J. Dermatol. Surg. Oncol.* 18:17-21, 1992. The clinical effects of peripheral intramuscular *Botulinum* toxin type A are usually seen within one week of injection. The typical duration of symptomatic relief from a single intramuscular injection of *Botulinum* toxin type A averages about three months. BTX-A serotype is available commercially for pharmaceutical use under the trademarks BOTOX™ (Allergan, Inc., Irvine, Calif., U.S.A.) and DYSPORT™ (Speywood Pharmaceuticals, Ltd., Maidenhead, U. K.). BOTOX™ consists of a purified *Botulinum* toxin type A complex, albumin and sodium chloride packaged in sterile, vacuum-dried form. Specifically, each vial of BOTOX™ contains about 100 Units (U) of *Clostridium botulinum* toxin type A purified neurotoxin complex, 0.5 milligrams of human serum albumin and 0.9 milligrams of sodium chloride in a sterile, vacuum-dried form without a preservative.

The *Botulinum* toxin type A is made from a culture of the Hall strain of *Clostridium botulinum* grown in a medium containing N-Z amine and yeast extract. The *Botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C.

BOTOX™ is sold in 100 Unit vials. DYSPORT™ is sold in 500 Unit vials. BTX-A is roughly tenfold less toxic than BOTOX™ and approximately fourfold greater amounts of the DYSPORT™ product will usually be injected to achieve the same result as would be obtained using a specific number of Units of BOTOX™.

For cosmetic uses, the vial contents are typically diluted with 1 or 2 ml of sterile saline solution, which for BOTOX™ provides a 100 or 50 Unit/ml dilution. (DYSPORT™ can also be utilized.) For example, BOTOX™ can be reconstituted with sterile, non-preserved saline prior to intramuscular injection. To reconstitute vacuum-dried BOTOX™, sterile normal saline without a preservative (0.9% Sodium Chloride Injection) is used by drawing up the proper amount of diluent in the appropriate size syringe. Since BOTOX™ may be denatured by bubbling or similar violent agitation, the diluent is gently injected into the vial. For sterility reasons BOTOX™ is preferably administered within four hours after the vial is removed from the freezer and reconstituted. During these four hours, reconstituted BOTOX™ can be stored in a refrigerator at about 2° C. to about 8° C. Reconstituted, refrigerated BOTOX™ has been reported to retain its potency for at least about two weeks (see *Neurology*, 48:249-53:1997).

Methods for Treatment of Depression

A method is provided herein for treating depression. The method includes administering a therapeutically effective amount of an agent (such as a neurotoxin) to a facial muscle involved in frowning, scowling, or a sad appearance. The agent causes partial or complete paralysis of the facial muscle, thereby affecting the ability of the subject to frown and/or scowl, or appear sad, and thereby treat depression. For example, a therapeutically effective amount of BTX can be injected into one or more of the orbicularis oculi, frontalis, procerus, the corrugator supercilii, or the depressor anguli oris (trianglaris muscle).

The method involves identifying or selecting persons who are depressed, and administering the treatment to them. Any form of depression can be treated herein, including mild depression, dysthymia and major depression. The depression can be the result of a mood disorder, and may be accompanied by an anxiety disorder. Without being bound by theory, decreased movement of muscles that contribute to the depressed facies helps elevate mood, and thus a lessening of the feeling of depression ensues. Denervation of the frown and scowl muscles results in a decreased ability of the treated subject to frown or scowl, and thus contributes to a subjective sense of elevated mood. Such improved mood can be objectively assessed by the DSM-IV criteria, or by standardized tests known in the art to determine whether a subject is depressed. Depression can be assessed, for example, by the *Beck Depression Inventory II* (1996, Harcourt). A very straightforward test is to ask the subject to report whether his or her mood has improved, or to rate feelings of depression on a numerical scale. Specific questions can also be asked about feelings of sadness and hopelessness, as well as changes in physical signs and symptoms associated with depression, such a neurovegetative complaints or psychomotor retardation.

The treatment can be repeated when the partial or complete muscle paralysis induced by the agent begins to abate. Alternatively, one can also wait for any signs or symptoms of depression to also recur after the muscular activity returns.

An exemplary injection technique involves the use of a short, narrow needle (e.g. ½ inch or 8 mm; 30-gauge) with an insulin- or tuberculin-type syringe. Subjects are typically treated in the seated position. The skin area is cleaned with an alcohol swab. A single syringe may be used for multiple injections to treat different locations in a single muscle or different locations on a patient's face. Typically, the plunger of the syringe is depressed as the needle is withdrawn so that toxin is evenly distributed at the injection site. Pressure or gentle massage may be applied at the injection site to assist in dissipating the toxin. The toxin will typically migrate approximately 1 cm from the site of injection.

Electromyographic (EMG) guided needles may be used for injection to determine needle location of a high degree of accuracy, although this technique is generally not necessary.

For applications of BTX, total dose per treatment can be varied and depends upon the condition being treated and the site of application of BTX. For example, a total dose of 10-50 Units (such as about 20 to about 40 Unit equivalents) will typically be applied to the glabellar complex and 60-75 Units for platysmal bands (Carruthers and Carruthers, *Dermatol. Surg.* 24:1168-1170, 1998). In one specific non-limiting example, about 30 to about 50 Unit equivalents of BTX is administered to the frontalis and/or the procerus muscle.

Onset of muscle paralysis following injection usually occurs within hours of treatment. The duration of paralysis will vary from patient to patient. Typically, duration will be from two to eight months, for example about three to about six months, or for example about three months, before subsequent treatment is required to alleviate the condition, although *Botulinum* toxin type A can have an efficacy for up to 12 months (Naumann et al., *European J. Neurology* 6(Supp 4):S111-S115, 1999).

Thus, in one specific, non-limiting example, to treat depression, a muscle involved in frowning or scowling is treated repeatedly. For example, about 30 to about 50 Unit equivalents of BTX is administered to the frontalis and/or the procerus muscle. After a period of about three months, and additional about 30 to about 50 Unit equivalents of BTX is administered to the corrugator supercilii, orbicularis oculi, procerus, and/or frontalis muscle. This treatment can be administered as many times as need to alleviate depression of the subject.

Figure 2:
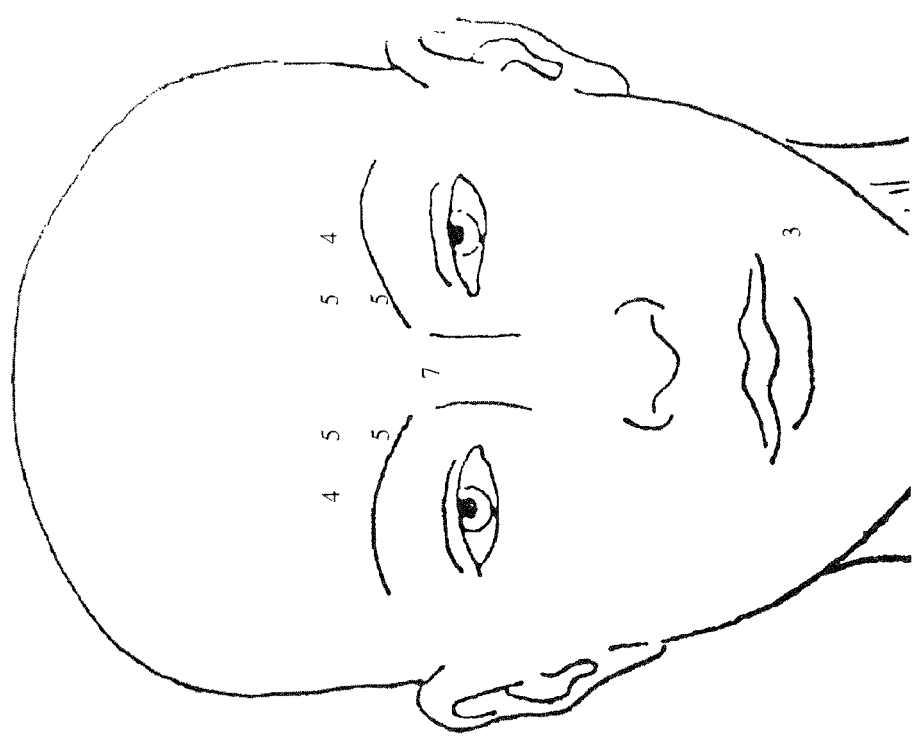
FIG. 2 is a schematic diagram of a typical *Botulinum* toxin dose used to treat frown lines and the depressor anguli oris in a man. In this specific, non-limiting example, about 35 Units are injected into the procerus, orbicularis oculi, and corrugator supercilii muscles. Numbers refer to the number of BTX Units per injection site.
Figure 3:
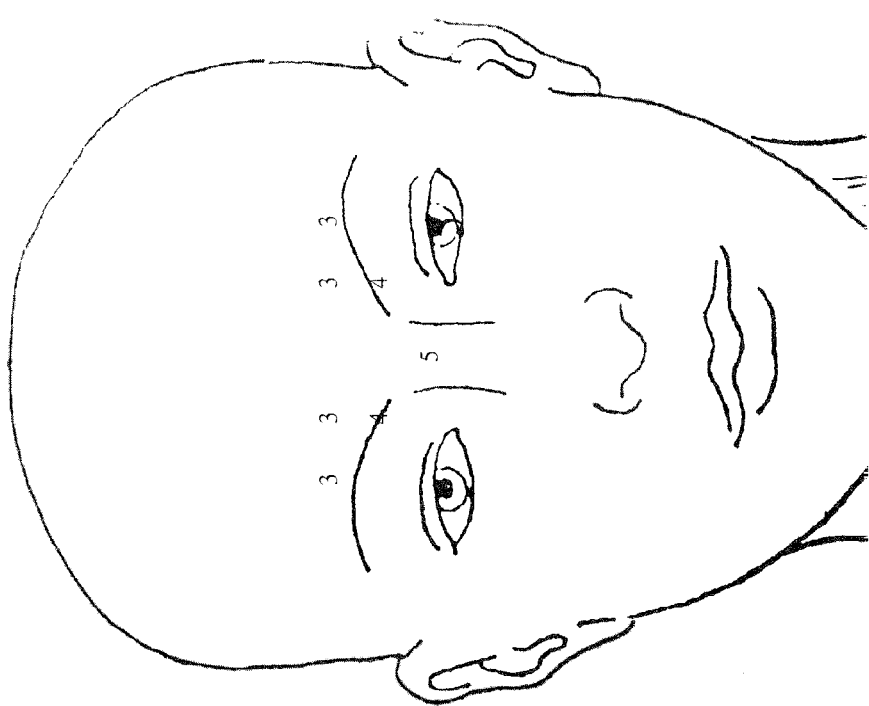
FIG. 3 is a schematic diagram of a typical *Botulinum* toxin dose used to treat frown lines in a woman. In this specific, non-limiting example, about 25 Units are injected into the procerus, orbicularis oculi, and corrugator supercilii muscles. Numbers refer to the number of BTX Units per injection site.

FIGS. 2 and 3 show *Botulinum* toxin dose used to treat the frown and/or scowl in a typical woman (FIG. 2) and man (FIG. 3). The landmarks for the injection are as follows (see also Carruthers et al., *Derm. Surg.* 24:1189-1194, 1998). The injection of the procerus is below a line joining the medial end of both eyebrows. The landmark for the next injections is a line vertically above the inner canthus and the superior margin of the orbit. *Botulinum* toxin is injected just superior to the first injection point. Next an injection is made 1 cm above the bone rim in the midpupullary line. The numbers refer to the number of BTX Units injected in the area shown.

In one specific, non-limiting example, for those patients with a sad appearance to their mouth, BTX is injected into the depressor anguli oris muscle. In such treatment, the orbicularis oris muscle surrounding the mouth is normally avoided in view of its sensitivity to BTX.

The depressor anguli oris can be found by instructing the patient to voluntarily and forcibly pull down the corners of the mouth. The depressor anguli oris can be then felt by pulling inferiorly at a point approximately 1 cm lateral and 8 mm inferior to the commissure. Alternatively, EMG localization may be performed.

Treatment should take into consideration the pre-existing symmetry of the mouth and is performed on both sides of the face in order to provide a symmetric result. The required dosage to each side of the mouth should be judged and if necessary, altered upon re-treatment.

Injection may be made into any part of the depressor anguli oris musculature. The injection is intramuscular and may be performed using the injection techniques used for other BTX treatments as described above. On a typical patient's face, an exemplary point of injection into the depressor anguli oris is approximately 1 cm laterally and 8 mm inferior from the corner of the mouth. A single injection will usually suffice with the dosage for a single depressor anguli oris muscle ranging from 3 (±10%) Units to 5 (±10%) Units. However, the dose depends upon the sex of the subject and size of the individual. Exemplary doses for a female are 2 (±10%) Units-3 (±10%) Units for one side of the mouth; and, for a male, 3 (±10%) Units to 5 (±10%) Units for one side of the mouth. Treatment generally does not affect normal speech, whistling or mastication particularly in cases where the orbicularis oris is not treated.

In one embodiment, a therapeutically effective amount of BTX is administered in combination with at least one additional modality of treatment for depression. The modality can be the administration of a therapeutically effective amount of an antidepressant. The modality of treatment can also be physical, such as electroconvulsive therapy, light therapy, or electromagnetic radiation. The modality can also be psychotherapy or exercise. A single modality of treatment can be combined with the BTX treatment, or a combination of additional modalities can be used with the BTX treatment. In particular examples, the additional modality is the administration of a therapeutically effective amount of an antidepressant medication, such as a tricyclic antidepressant or a selective serotonin reuptake inhibitor (SSRI), or other classes of drugs (such as an MAOI or a tricyclic antidepressant). The BTX can be administered simultaneously or sequentially with the additional modality of treatment. Thus, in one example, a subject taking a therapeutically effective amount of an antidepressant medication (such as an SSRI), or undergoing a therapeutic protocol, can be treated with BTX during the course of the additional treatment. Alternatively, BTX can be administered after the treatment has been terminated, or prior to the initiation of therapy, such as the administration of the antidepressant medication, psychotherapy, or a physical treatment protocol. In one specific example, BTX is administered to a subject who is also taking a therapeutically effective amount of an SSRI.

This disclosure is illustrated by the following non-limiting Examples.

EXAMPLES

Example 1

Patient 1

Figure 4:
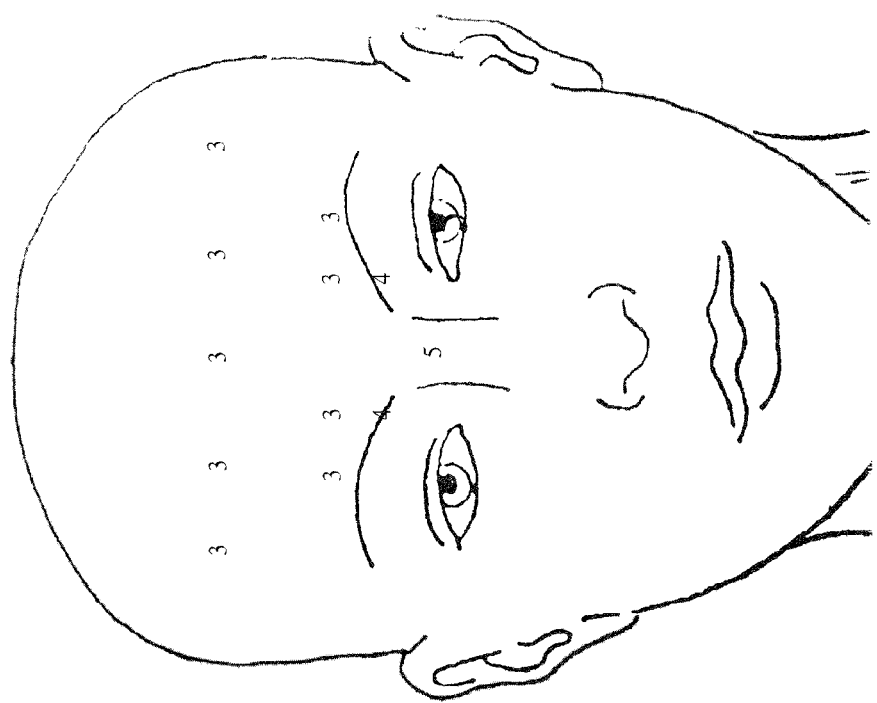
FIG. 4 is a schematic diagram of a *Botulinum* toxin dose used to treat patient 1. The numbers shown indicate the number of Units of *Botulinum* toxin injected. In this example, about 40 Units are injected into the procerus, orbicularis oculi, and corrugator supercilii muscles. Numbers refer to the number of BTX Units per injection site.

A 59-year-old Caucasian female with a history of depression for 3 years was treated. Medications included PAXIL® (20 mg), as prescribed by her psychiatrist. She appeared somewhat depressed at the time of the first office visit. Her glabellar frown lines and forehead lines were treated with 40 i.u. of BOTOX™ (FIG. 4).

Three months later the patient returned for re-treatment. The patient stated that she no longer felt depressed and she attributed her improvement in her mood to the BOTOX™. Her glabellar frown lines and forehead lines were treated with 40 i.u. of BOTOX™. In a telephone follow-up interview two months later, the patient reported feeling well and that she was no longer depressed.

This example illustrates that BOTOX™ injection can be used in combination with other treatment modalities (such as antidepressant medications, for example tricyclic antidepressants, serotonin specific reuptake inhibitors (SSRIs), norepinephrine reuptake inhibitors, monoamine oxidase inhibitors (MAOIs), and others). It is also anticipated that the injection could be used in combination with other therapies, such as psychotherapy.

Example 2

Patient 2

A 33-year-old Caucasian female with a history of intermittent anxiety/depression for ten years was treated. Her medications included an SSRI (ZOLOFT®, 200 mg per day) for the last four years. Prior to treatment she reported feeling depressed and anxious.

Figure 5:
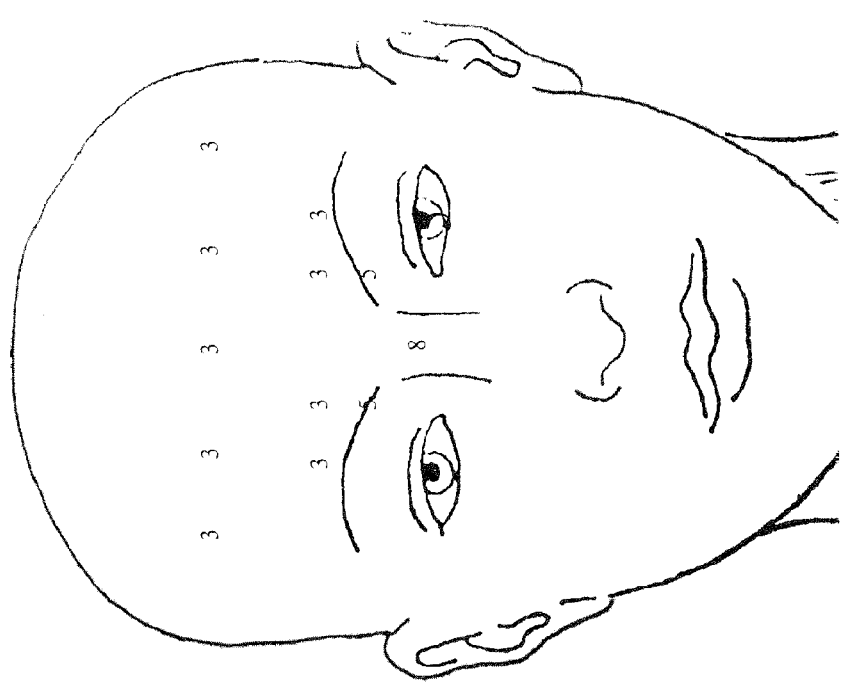
FIG. 5 is a schematic diagram of a *Botulinum* toxin dose used to treat patient 2. The numbers shown indicate the number of Units of *Botulinum* toxin injected. In this example, about 30 Units are injected into the procerus, orbicularis oculi, and corrugator supercilii muscles. Numbers refer to the number of BTX Units per injection site.

Her frown/glabellar lines were injected with 30 Unit equivalents of BOTOX™ (FIG. 5). Three months later she returned to the office for a follow-up appointment. She stated that she felt happier during the last couple of months than she had in years. Her frown/glabellar lines were re-treated at that time with 30 Unit equivalents of BOTOX™.

Example 3

Patient 3

A 50-year-old, recently divorced, Caucasian female was treated. She had a history of depression for two years. Her medications included PAXIL® 20 mg orally per day and WELLBUTRIN® 225 mg orally per day. She reported feeling depressed.

Figure 6:
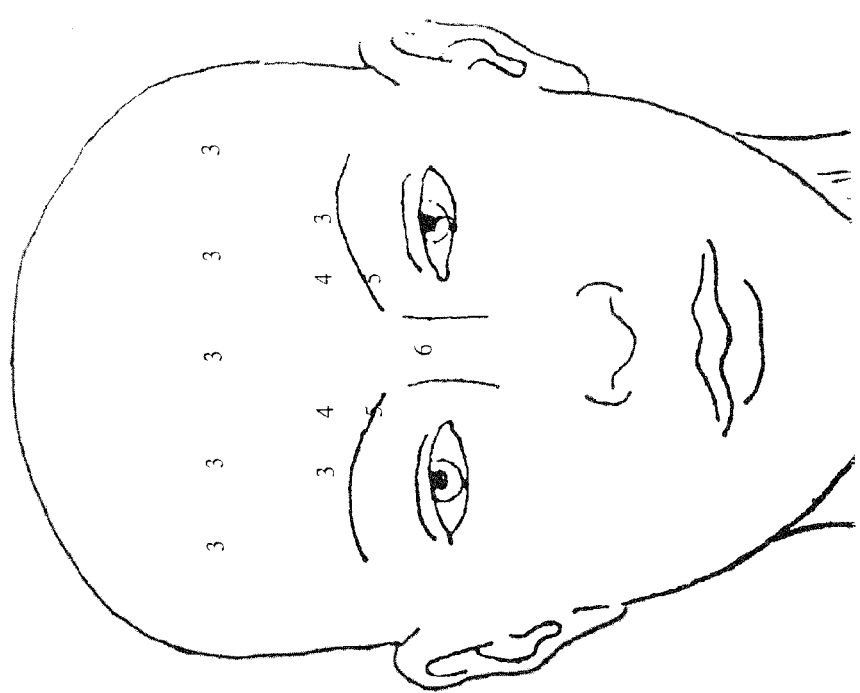
FIG. 6 is a schematic diagram of a *Botulinum* toxin dose used to treat patient 3. The numbers shown indicate the number of Units of *Botulinum* toxin injected. In this example, about 30 Units are injected into the procerus, orbicularis oculi, and corrugator supercilii muscles. Numbers refer to the number of BTX Units per injection site.

Her frown/glabellar lines were injected with 30 Unit equivalents of BOTOX™ (FIG. 6). Four months later she reported a much-improved mood, and stated that she did not feel depressed. Her frown/glabellar lines were re-treated with 30 Unit equivalents of BOTOX™.

Example 4

Patient 4

A 63 year-old Caucasian female had a history of a moderately severe chronic depression for 20 years. During the past twenty years she had undergone treatment with various combinations of SSRI's and tricyclic antidepressants. Her medications at the time of her first office visit included an SSRI, ZOLOFT®, 200 mg orally per day and WELLBUTRIN® 225 mg orally per day, as prescribed by her psychiatrist. She was evaluated by the Beck Depression Inventory (1996, Harcourt). Her pretreatment score was 27, indicative of an ongoing major clinical depression. Physical exam revealed very prominent frown lines.

She was treated with 30 Unit equivalents of BOTOX™ injected into her glabellar frown lines. At follow-up 6 weeks later she stated that she had not felt this well in years. Objective evaluation revealed a follow-up score of 5 on the Beck's scale, indicating that she was no longer clinically depressed.

It will be apparent that the precise details of the methods or compositions described may be varied or modified without departing from the spirit of the described invention. I claim all such modifications and variations that fall within the scope and spirit of the claims below.

I claim:

1. A method for treating dysthymia, major depression or a mood disorder in a subject, comprising:
   administering a therapeutically effective amount of a composition comprising a *botulinum* toxin to one or more facial muscle involved in frowning, scowling or a sad appearance; wherein the therapeutically effective amount is an amount sufficient to cause paralysis of the one or more facial muscle;
   thereby treating dysthymia, major depression or a mood disorder in the subject.

2. The method of claim 1, wherein the one or more facial muscle involved in frowning, scowling or a sad appearance is selected from the group consisting of frontalis, orbicularis oculi, procerus, corrugator supercilii, and depressor anguli oris muscle.

3. The method of claim 1, wherein the one or more facial muscle is a frontalis muscle, an orbicularis oculi muscle, or a procerus muscle.

4. The method of claim 1, wherein the one or more facial muscle is a corrugator supercilii muscle, or a procerus muscle.

5. The method of claim 1, wherein the *botulinum* toxin in the composition is selected from the group consisting of the *botulinum* toxins types A, B, $C_1$, D, E, F and G.

6. The method of claim 5, wherein the *botulinum* toxin in the composition is *botulinum* toxin A.

7. The method of claim 1, wherein the therapeutically effective amount is about 5-60 Unit equivalents of a *botulinum* toxin type A.

8. The method of claim 7, further comprising administering a second composition comprising an additional therapeutically effective amount of the *botulinum* toxin type A to the one or more facial muscle after about two to six months.

9. The method of claim 1, further comprising administering to the subject a therapeutically effective amount of an additional modality of treatment for depression.

10. The method of claim 9, wherein the additional modality of treatment comprises administration of an antidepressant, psychotherapy, or a physical treatment for depression.

11. The method of claim 9, wherein the additional modality of treatment comprises a selective serotonin reuptake inhibitor.

\* \* \* \* \*